(12) United States Patent
Rogers et al.

(10) Patent No.: US 10,532,046 B2
(45) Date of Patent: Jan. 14, 2020

(54) MULTI-PHASE DELIVERY COMPOSITIONS AND PRODUCTS INCORPORATING SUCH COMPOSITIONS

(71) Applicant: Niconovum USA, Inc., Winston-Salem, NC (US)

(72) Inventors: James William Rogers, Winston-Salem, NC (US); Michael F. Davis, Clemmons, NC (US); Percy D. Phillips, Pfafftown, NC (US); Karen V. Taluskie, Winston-Salem, NC (US); Stephen Benson Sears, Siler City, NC (US); Ercilia Hernandez Garcia, Clayton, NC (US)

(73) Assignee: Niconovum USA, Inc., Winston-Salem, NC (US)

( * ) Notice: Subject to any disclaimer, the term of this patent is extended or adjusted under 35 U.S.C. 154(b) by 0 days.

(21) Appl. No.: 14/958,555

(22) Filed: Dec. 3, 2015

(65) Prior Publication Data
US 2017/0157106 A1    Jun. 8, 2017

(51) Int. Cl.
| | |
|---|---|
| A61K 9/70 | (2006.01) |
| A61K 31/465 | (2006.01) |
| A61K 9/00 | (2006.01) |
| A24F 23/00 | (2006.01) |
| A24D 3/06 | (2006.01) |
| A24D 3/04 | (2006.01) |
| A23L 27/00 | (2016.01) |
| A61K 9/68 | (2006.01) |
| A24B 13/00 | (2006.01) |
| A24B 15/16 | (2006.01) |
| A24B 15/18 | (2006.01) |
| A24B 15/28 | (2006.01) |
| A24D 1/00 | (2006.01) |
| A24D 1/02 | (2006.01) |
| A24F 15/00 | (2006.01) |
| A24F 47/00 | (2006.01) |

(52) U.S. Cl.
CPC ............ *A61K 31/465* (2013.01); *A24B 13/00* (2013.01); *A24B 15/16* (2013.01); *A24B 15/186* (2013.01); *A24B 15/282* (2013.01); *A24D 1/002* (2013.01); *A24D 1/025* (2013.01); *A24D 3/048* (2013.01); *A24D 3/061* (2013.01); *A24F 15/00* (2013.01); *A24F 23/00* (2013.01); *A24F 47/006* (2013.01); *A24F 47/008* (2013.01); *A61K 9/0053* (2013.01); *A61K 9/7007* (2013.01)

(58) Field of Classification Search
None
See application file for complete search history.

(56) References Cited

U.S. PATENT DOCUMENTS

| | | | |
|---|---|---|---|
| 4,347,324 A | 8/1982 | Wildman et al. | |
| 4,579,858 A | 4/1986 | Fernö et al. | |
| 4,780,309 A | 10/1988 | Geria et al. | |
| 6,238,689 B1 | 5/2001 | Rhodes et al. | |
| 6,340,471 B1 | 1/2002 | Kershman et al. | |
| 6,344,222 B1 | 2/2002 | Cherukuri et al. | |
| 6,692,771 B2 * | 2/2004 | Pather | A61K 9/143 424/458 |
| 7,056,541 B1 | 6/2006 | Stahl | |
| 8,679,522 B2 * | 3/2014 | Barreca | A23G 3/362 424/439 |
| 2004/0096498 A1 | 5/2004 | Kershman et al. | |
| 2006/0073190 A1 * | 4/2006 | Carroll | A23G 3/343 424/440 |
| 2006/0120974 A1 | 6/2006 | Mcneight | |
| 2007/0104778 A1 * | 5/2007 | Zeng | A61K 9/1075 424/451 |
| 2007/0269417 A1 | 11/2007 | McNeight | |
| 2008/0253976 A1 * | 10/2008 | Scott | A61K 8/0216 424/49 |
| 2008/0260807 A1 * | 10/2008 | Sharp | A61K 9/006 424/443 |
| 2009/0139533 A1 | 6/2009 | Park et al. | |
| 2010/0260835 A1 * | 10/2010 | Wheeler | A61K 9/0031 424/455 |
| 2011/0305768 A1 * | 12/2011 | Mao | A61K 39/15 424/499 |
| 2015/0313285 A1 | 11/2015 | Waller et al. | |

OTHER PUBLICATIONS

Hawley's Online; definition for "emulsion"; (onlinelibrary.wiley.com/doi/10.1002/9780470114735.hawley06483); published Mar. 15, 2007; downloaded Jan. 17, 2019.*
www.ecigarette-research.com/web/index.php/2013-04-07-09-50-07-2014/157-glycerol, Dr. Farsalinos: "Doctors, open your textbooks: Glycerol Cannot Cause Lipoid Pneumonia (But Other Things Can)," Ecigarette Research, Mar. 14, 2014. Retrieved from Internet on Jan. 24, 2017.

* cited by examiner

*Primary Examiner* — Jeffrey T. Palenik
(74) *Attorney, Agent, or Firm* — Womble Bond Dickinson (US) LLP

(57) ABSTRACT

The present disclosure relates to compositions that are useful in the delivery of various materials. In particular, the compositions comprise a suspension wherein an internal phase material is surrounded by an external phase material. The internal phase specifically can be a hydrophilic material, and the external phase specifically can be a hydrophobic material. The materials are combined so that the internal phase is substantially encapsulated by the external phase such that release can be controlled in relation to osmotic pressure differentials. The suspension can be combined with a carrier, and various systems and products can be formed with the suspension and optional carrier, such as oral strips, spray delivery systems, smokeless tobacco products, aerosol delivery devices, cigarettes, and packaging.

18 Claims, 9 Drawing Sheets

MULTI-PHASE DELIVERY COMPOSITIONS AND PRODUCTS INCORPORATING SUCH COMPOSITIONS

TECHNICAL FIELD

The present disclosure relates to compositions that can be configured for delivery of one or more materials as part of an internal phase that is present within an external phase lipid material. The compositions particularly can provide for controlled release of the internal phase material and can find use in a variety of fields, including but not limited to nicotine replacement products.

BACKGROUND

Many different compositions have been proposed for use in delivery of one or more desired materials. For example, in the field of nicotine replacement products, many compositions have been proposed for delivery of the nicotine in a variety of manners, particularly in an effort to help cigarette smokers quit smoking (i.e., as a smoking cessation aid). For example, nicotine has been an active ingredient of various types of so-called "nicotine replacement therapy" or "NRT" products. See, for example, U.S. patent application Ser. No. 12/769,335 and International Application No. PCT/US2011/033928, both to Brinkley et al., which are incorporated herein by reference.

In some exemplary uses, it has been proposed to administer active agents, such as nicotine, using a transdermal patch. Representative types of nicotine-containing transdermal patch products have been marketed under the tradenames "Habitrol," "Nicoderm," "Nicorette," "Nicorette CQ," "Nicotinell" and "Pro Step." See also, for example, U.S. Pat. No. 4,597,961 to Etscom; U.S. Pat. No. 5,298,257 to Bannon et al.; U.S. Pat. No. 5,603,947 to Wong et al.; U.S. Pat. No. 5,834,011 to Rose et al.; U.S. Pat. No. 6,165,497 to Osborne et al, and U.S. Pat. No. 6,676,959 to Anderson et al. It also has been suggested that transdermal administration of nicotine can be supplemented with or replaced by ingestion of other types of nicotine-containing products. See, for example, U.S. Pat. No. 5,593,684 to Baker et al.; US Pat. Pub. No. 2009/0004249 to Gonda; and Fagerstrom, Health Values, 18:15 (1994).

One particularly popular way to provide for oral administration of nicotine has been through the use of nicotine-containing gum. Nicotine-containing gum products have been marketed under the tradenames "Nicorette," "Nicotinell" and "Zonnic." Another way that has been employed to provide oral administration of nicotine has been through the use of nicotine-containing lozenge or tablet types of products. Nicotine-containing lozenge, mini lozenge, tablet, and microtab types of products have been marketed under the tradenames "Commit," "Nicorette," "Nicotinell" and "NiQuitin." Nicotine also has been administered in the form of nasal or oral sprays. Nicotine-containing sprays have been marketed under the tradenames "Nicotrol NS," "Quit" and "Zonnic."

Various other ways to administer nicotine for the purpose of providing a therapeutic effect have been proposed. For example, it has been suggested that nicotine can be incorporated into orally dissolving films (e.g., U.S. Pat. No. 6,709,671 to Zerbe et al.); oral osmotic devices (e.g., U.S. Pat. No. 5,147,654 to Place et al.); gum pads (e.g., U.S. Pat. No. 6,319,510 to Yates); oral patches (e.g., US Pat. Pub. No. 2006/0240087 to Houze et al.); snuff-type forms in pouches or sachets (e.g., U.S. Pat. No. 4,907,605 to Ray et al. and US Pat. Pub, No. 2009/0293895 to Axelsson et al.); lip balm (e.g., U.S. Pat. No. 7,105,173 to Rolling) and beverages (e.g., U.S. Pat. No. 6,268,386 to Thompson; U.S. Pat. No. 7,115,297 to Stillman and U.S. Pat. No. 7,435,749 to Knight). It also has been suggested that nicotine can be delivered using various types of inhalation devices and vapor delivery systems. See, for example, the various alternative smoking articles, aerosol delivery devices, and heat generating sources set forth in the background art described in U.S. Pat. No. 7,726,320 to Robinson et al., U.S. Pat. Pub. No. 2013/0255702 to Griffith Jr. et al., and U.S. Pat. Pub. No. 2014/0096781 to Sears et al., all of which are incorporated herein by reference.

Although the foregoing specifically relates to delivery of nicotine, in a similar manner, these and other means have been utilized for delivery of other materials, such as other flavoring materials. Nevertheless, there remains a need for additional means for delivery of materials, particularly in a controlled manner and for a variety of uses.

SUMMARY OF THE DISCLOSURE

The present disclosure relates to compositions and systems suitable for delivery of a material. Delivery may be to a consumer. Delivery may relate to delayed release of the material. The delivery compositions and systems particular can comprise a suspension of the material for release within an encapsulating layer. More particularly, the material for delivery can be an internal phase that is substantially completely surrounded by an external phase material. Preferably, the internal phase can be substantially hydrophilic, and the external phase can be substantially hydrophobic. As such, release of the internal phase material can be driven substantially by osmotic pressure differentials between the internal phase material and a surrounding environment.

In certain aspects, the present disclosure can provide a delivery composition. In some embodiments, a delivery composition can comprise a carrier and a suspension having an external phase comprising a lipid and an internal phase comprising a substantially hydrophilic material. In particular, the internal phase material can be selected from the group consisting of nicotine, flavorants, humectants, tobacco extracts, water, and combinations thereof. In various embodiments, a delivery composition can be further defined by one or more of the following statements, any number of which may be utilized in any desired combination.

The internal phase material can be a liquid.
The suspension can be bioadhesive.
The carrier can be a liquid.
The carrier can be a solid.
A solid carrier can be dissolvable under mouth conditions.
A solid carrier can be a gum or a lozenge.
A solid carrier can be an oral thin film.
An oral thin film can be a layered construct comprising a first thin film, a second thin film, and the suspension positioned between the first thin and the second thin film.
In a layered construct, one of the first thin film and the second thin film can be dissolvable under mouth conditions and the other can be substantially non-dissolvable under mouth conditions.
In a layered construct, both of the first thin film and the second thin film can be dissolvable under mouth conditions and, under the same mouth conditions, one of the first thin film and the second thin film can dissolve at a rate that is faster than the other by a rate of about 10% or greater.
The suspension can be dispersed in an oral thin film.

The carrier can be a sprayable or pumpable liquid, and the suspension can be in admixture with the sprayable or pumpable liquid and housed in a spray or pump device.

The carrier can be a smokeless tobacco material.

A smokeless tobacco material can be enclosed within a fleece.

The carrier can be a smokeless tobacco substitute.

The internal phase material can be encapsulated within an encapsulating layer.

The suspension can be configured for controlled release of the internal phase from the external phase based upon an osmotic pressure differential between the internal phase and a site of delivery.

An osmotic pressure differential can be between the internal phase and saliva in the mouth of a user.

The composition can be stable such that after a storage time of 3 months, the rate of release of the nicotine from the composition changes by about 5% or less.

In certain aspects, the present disclosure can provide an oral strip. In some embodiments, an oral strip can comprise at least a first thin film and a suspension having an external phase comprising a lipid and an internal phase comprising a substantially hydrophilic material. In particular, the internal phase material can be selected from the group consisting of nicotine, flavorants, humectants, tobacco extracts, and combinations thereof. In some embodiments, the suspension can be dispersed in the at least one first thin film. In some embodiments, the oral strip can comprise a first thin film and second thin film, and the suspension can be positioned between the first thin and the second thin film. In some embodiments, the suspension can be positioned within the second thin film.

In certain aspects, the present disclosure can provide a spray delivery system. In some embodiments, a spray delivery system can comprise: a container configured for spraying a liquid contained therein; a sprayable liquid carrier housed within the container; and a suspension intermixed with the sprayable liquid carrier, the suspension having an external phase comprising a lipid and an internal phase comprising a substantially hydrophilic material. In particular, the internal phase material can be selected from the group consisting of nicotine, flavorants, humectants, tobacco extracts, and combinations thereof.

In certain aspects, the present disclosure can provide a smokeless tobacco product. In some embodiments, a smokeless tobacco product can comprise a smokeless tobacco material and a dressing material that is a suspension having an external phase comprising a lipid and an internal phase comprising a substantially hydrophilic material. In particular, the internal phase material can be selected from the group consisting of nicotine, flavorants, humectants, tobacco extracts, water, and combinations thereof. In some embodiments, the smokeless tobacco material can comprise a natural tobacco material. In some embodiments, the smokeless tobacco material can comprise a smokeless tobacco substitute. Natural tobacco and/or a tobacco substitute can be in a particulate form (e.g., shredded, ground, powdered, etc.).

In certain aspects, the present disclosure can provide an aerosol delivery device. In some embodiments, an aerosol delivery device can comprise: an air inlet; a mouthend positioned downstream from the air inlet; a heat source positioned upstream from the mouth end: an air flow stream between the heat source and the mouthend; and a carrier element positioned in the air flow stream between the heat source and the mouthend, the carrier element carrying a suspension having an external phase comprising a lipid and an internal phase comprising a substantially hydrophilic material. In particular, the internal phase material can be selected from the group consisting of nicotine, flavorants, humectants, tobacco extracts, water, and combinations thereof. In some embodiments, the heat source can be an electric heater. In some embodiments, the aerosol delivery device can further comprise an aerosol precursor composition and a liquid transport element configured for transport of the aerosol precursor composition to an electric heater. In some embodiments, the heat source can be a fuel element. In some embodiments, the carrier element can comprise a tobacco material.

In certain aspects, the present disclosure can provide a smoking article—e.g., a cigarette. In some embodiments, a cigarette can comprise a tobacco rod, a filter element connected to the tobacco rod, and a suspension having an external phase comprising a lipid and an internal phase comprising a substantially hydrophilic material. In particular, the internal phase material can be selected from the group consisting of nicotine, flavorants, humectants, tobacco extracts, water, and combinations thereof. In some embodiments, the suspension can be incorporated into the tobacco rod. In some embodiments, the suspension can be incorporated into the filter element. In some embodiments, the suspension can be provided within a breakable capsule.

In certain aspects, the present disclosure can provide elements associated with packaging. In particular, the packaging can be for a tobacco product. In some embodiments, packaging for a tobacco product can comprise a container having at least one wall with an inner surface, the container being configured for containing the tobacco product, and a suspension having an external phase comprising a lipid and an internal phase comprising a substantially hydrophilic material. In particular, the internal phase material can be selected from the group consisting of nicotine, flavorants, humectants, tobacco extracts, water, and combinations thereof. In particular, the suspension is present within the container. In various embodiments, packaging can be further defined by one or more of the following statements, any number of which may be utilized in any desired combination.

The container can be a cigarette container.

The container can be a smokeless tobacco container.

The container can comprise at least one wall with an inner surface.

The packaging of claim 40, wherein the suspension can be coated on at least a portion of the inner surface of the at least one wall.

The suspension can be retained in or on a carrier.

The carrier can be attached to the inner surface of the at least one wall.

BRIEF DESCRIPTION OF THE DRAWINGS

Figure 1:
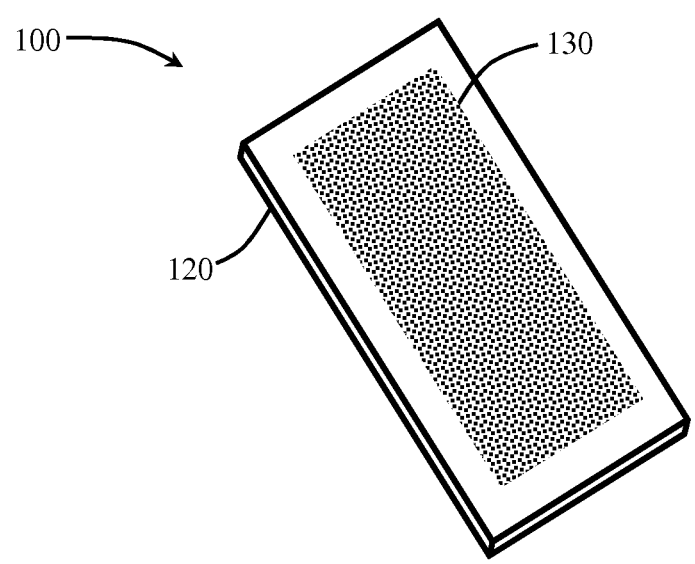
Figure 2:
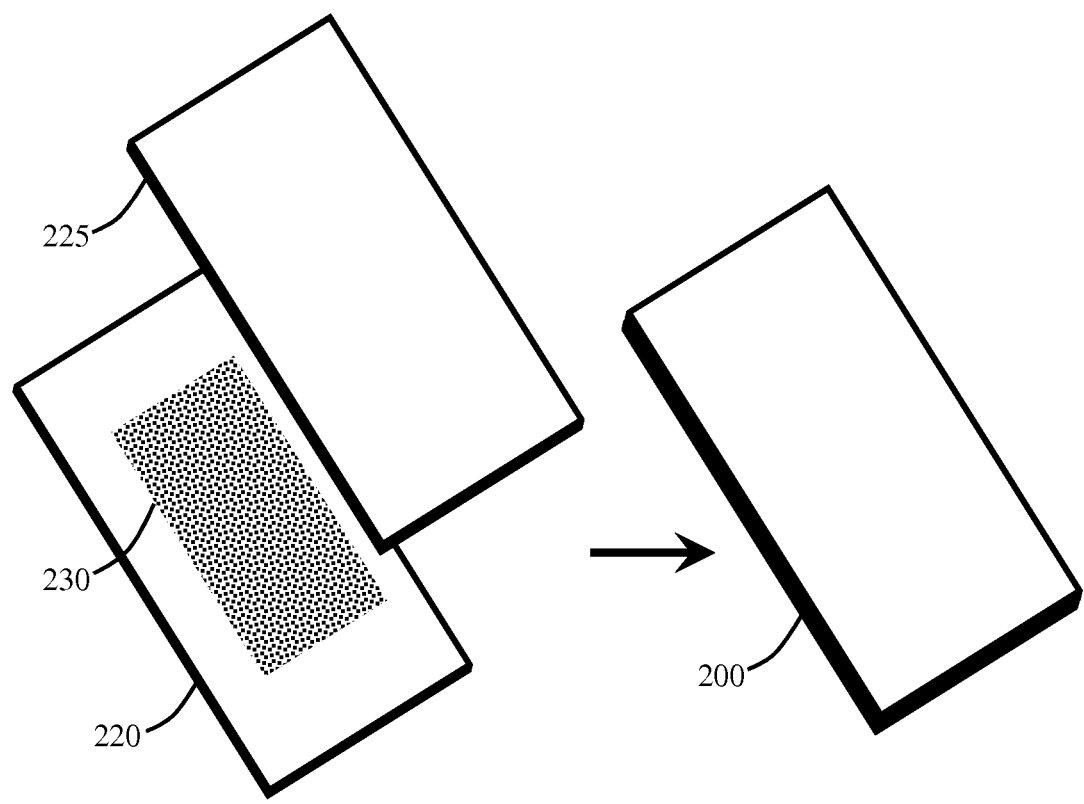
Figure 3:
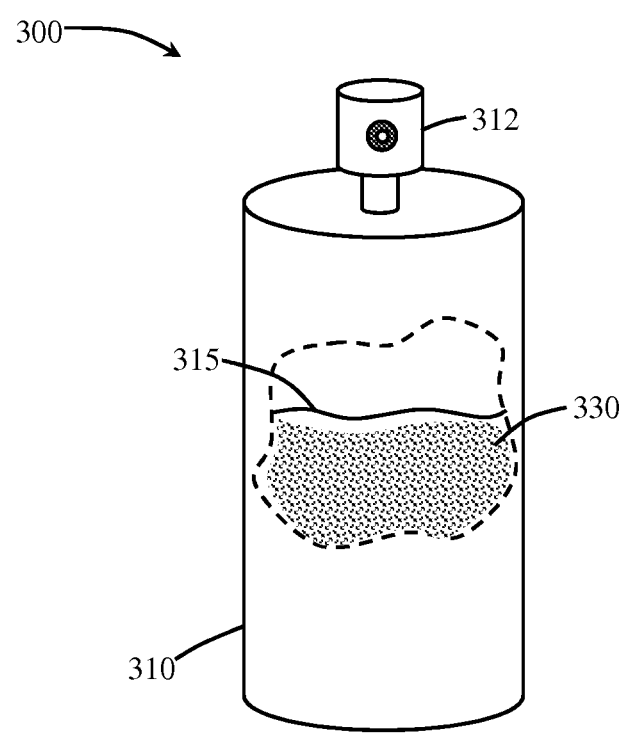
Figure 4:
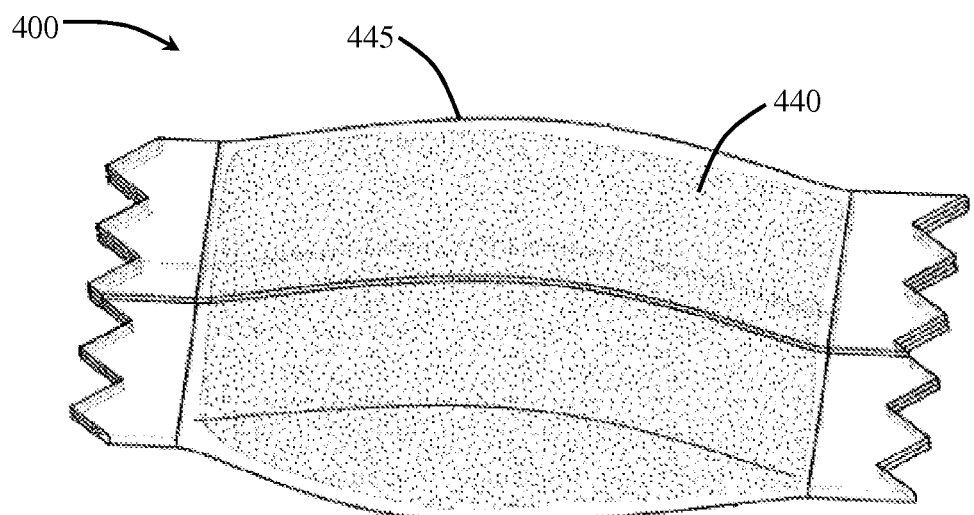
Figure 5:
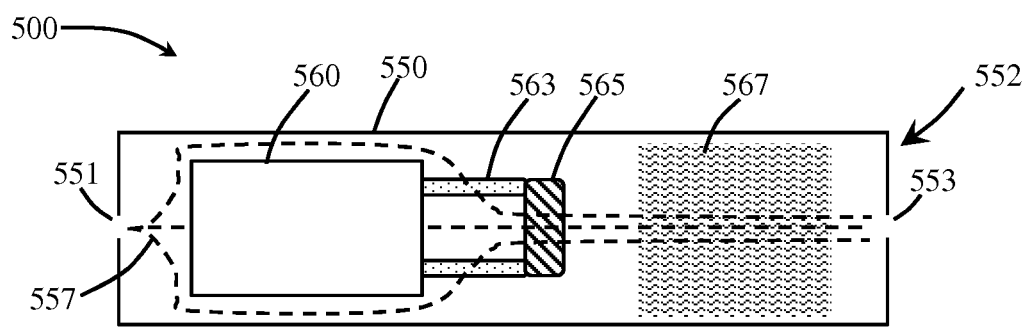
Figure 6:
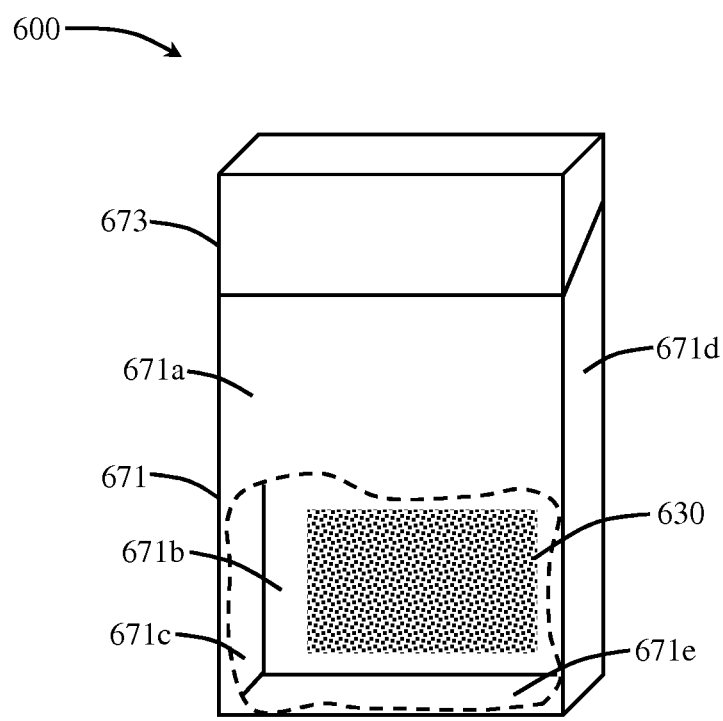
Figure 7:
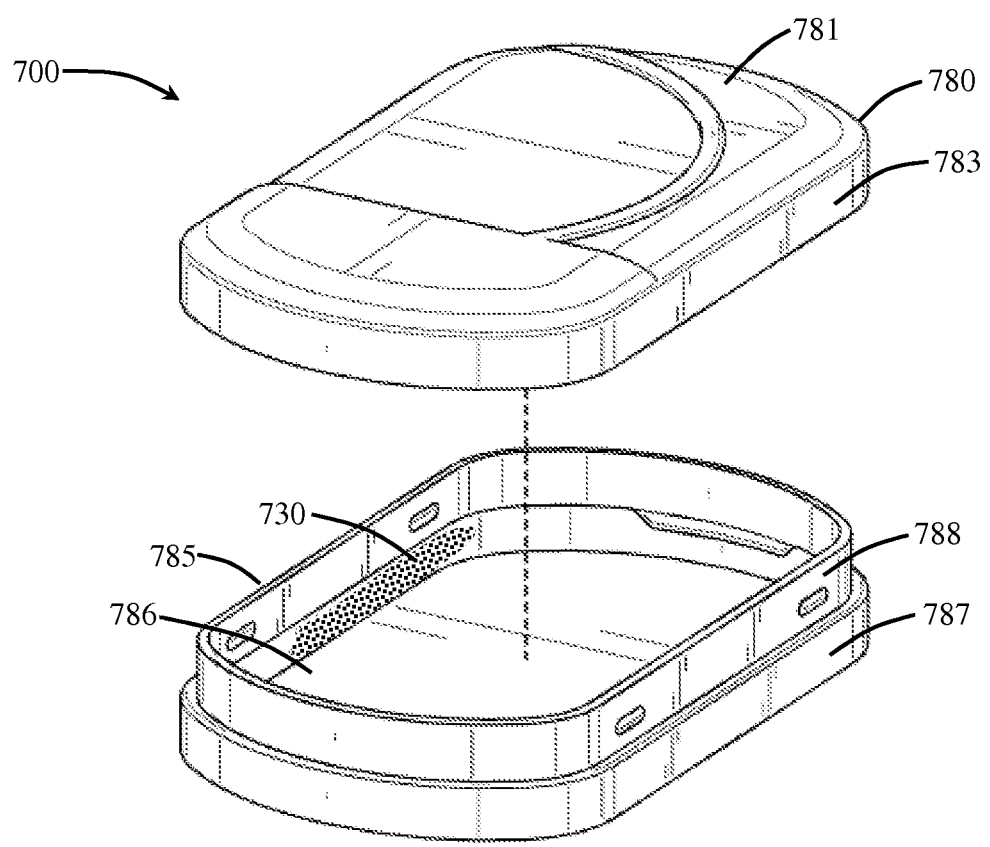
Figure 8:
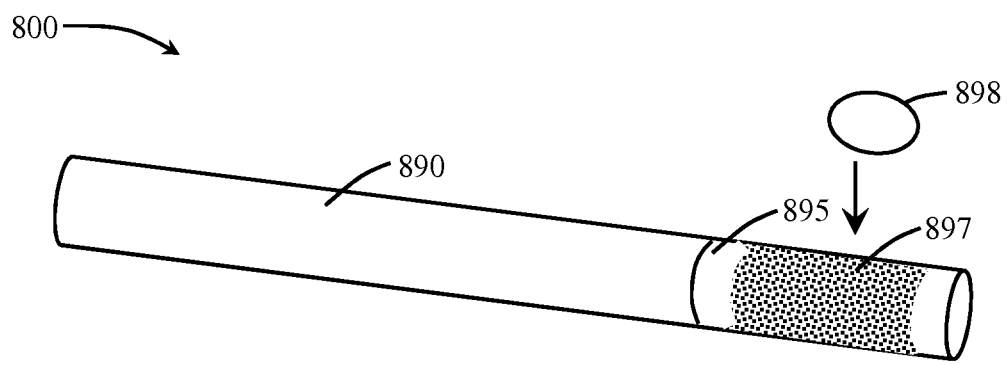
Figure 9:
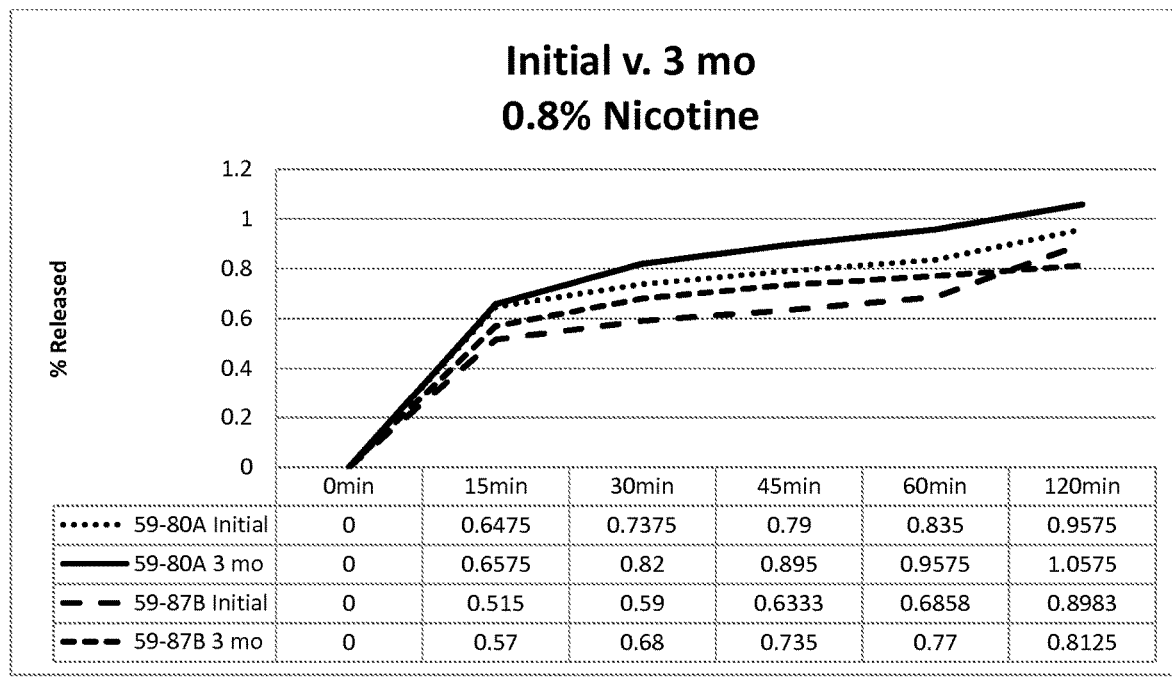
Figure 10:
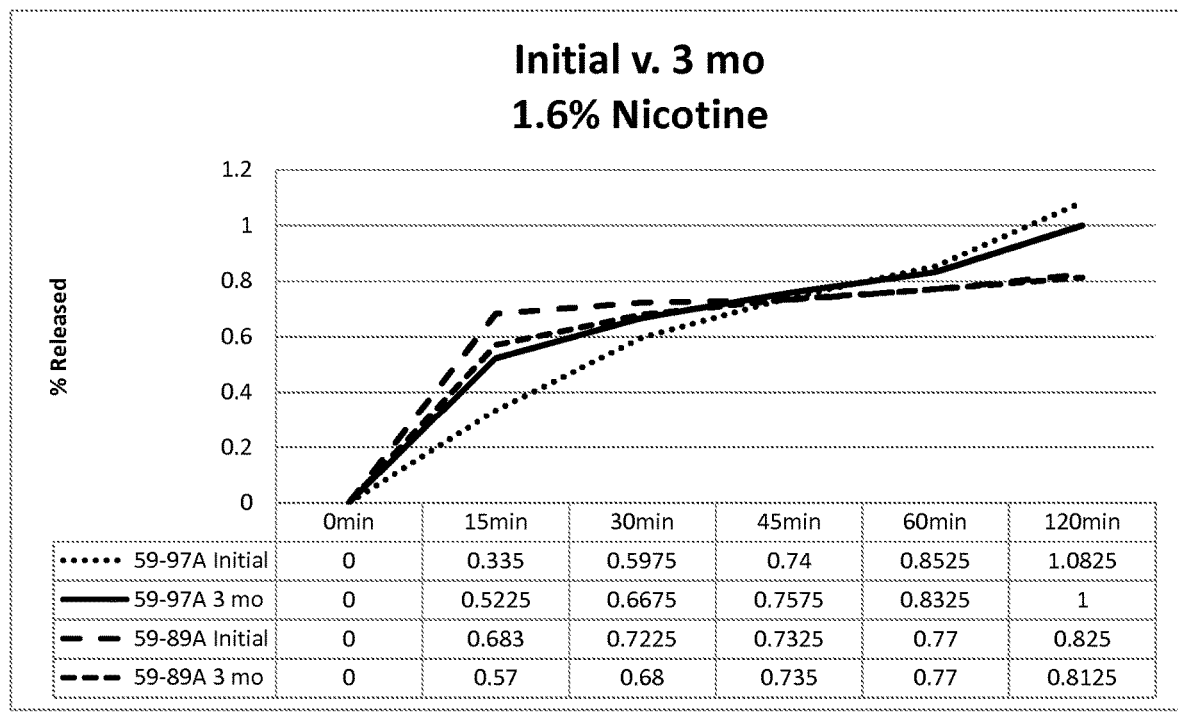

Having thus described the disclosure in the foregoing general terms, reference will now be made to the accompanying drawings, which are not necessarily drawn to scale, and wherein:

FIG. 1 illustrates a thin film including a suspension according to exemplary embodiments of the present disclosure, the thin film being suitable for use as an oral strip;

FIG. 2 illustrates the combination of two thin films with a suspension according to exemplary embodiments of the present disclosure, the combination of thin films being suitable for use as an oral strip;

FIG. 3 illustrates a spray bottle including a sprayable liquid carrier and a suspension according to exemplary embodiments of the present disclosure, the combination of elements forming a spray system suitable for spray delivery of the suspension;

FIG. 4 illustrates a pouch material in which a tobacco material or tobacco substitute material is provided and which includes a suspension according to exemplary embodiments of the present disclosure, the combination of elements being suitable for use as a smokeless tobacco product;

FIG. 5 illustrates an aerosol delivery device that includes a suspension according to exemplary embodiments of the present disclosure, the combination of elements being suitable for use in providing an aerosol that incorporates at least a portion of the suspension therein;

FIG. 6 illustrates a cigarette package that includes a suspension according to exemplary embodiments of the present disclosure, the suspension being included on an inner surface of a wall of the package;

FIG. 7 illustrates a smokeless tobacco container that includes a suspension according to exemplary embodiments of the present disclosure, the suspension being included on an inner surface of a wall of the container;

FIG. 8 illustrates a smoking article that includes a suspension according to exemplary embodiments of the present disclosure, the suspension being included on a filter portion of the smoking article;

FIG. 9 is a graph showing a comparison of the release rate of nicotine from a suspension according to exemplary embodiments of the present disclosure after preparation of the suspension and after storage at room temperature for 3 months; and FIG. 10 is a graph showing a comparison of the release rate of nicotine from a suspension according to exemplary embodiments of the present disclosure after preparation of the suspension and after storage at room temperature for 3 months.

DETAILED DESCRIPTION OF THE DISCLOSURE

The present disclosure relates to compositions that can be utilized in the delivery of a variety of materials. Such delivery compositions particularly can be utilized in relation to tobacco product and/or for delivery of a tobacco-related material, including but not limited to nicotine.

In some embodiments, the delivery composition particularly can comprise a suspension wherein a material for delivery can be provided as an internal phase that is substantially suspended within an external phase material. Preferably, the internal phase material is a hydrophilic material. In specific embodiments, the internal phase material can include one or more of nicotine, flavorants, humectants, tobacco extracts, and water.

As used herein, "nicotine" can refer to naturally occurring or synthetic nicotine unbound from a plant material, meaning the compound is at least partially purified and not contained within a plant structure such as a tobacco leaf. Most preferably, the nicotine is naturally-occurring and obtained as an extract from a *Nicotiana* species (e.g., tobacco). Exemplary types of tobacco and manners of processing the tobacco are set forth in U.S. patent application Ser. No. 13/095,277 to Byrd et al., which is incorporated herein by reference.

The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis. Despite the fact that nicotine can be extracted from *Nicotiana* species, in some embodiments the nicotine (and the composition and products produced in accordance with the present invention) can be virtually, essentially, or substantially free of other components of tobacco.

In embodiments wherein nicotine is derived from a plant of the *Nicotiana* species, the plant or portions thereof can be subjected to various types of processing conditions to provide the nicotine. For example, components can be separated from one another, or otherwise fractionated into chemical classes or mixtures of individual compounds. Typical separation processes can include one or more process steps (e.g., solvent extraction using polar solvents, organic solvents, or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), diethyl ether methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., LC-GC Europe, p. 2-5 (March, 2002) and Wellings, A Practical Handbook of Preparative HPLC (2006), which are incorporated herein by reference. In addition, the plant or portions thereof can be subjected to the types of treatments set forth in Ishikawa et al., Chem, Pharm, Bull., 50, 501-507 (2002); Tienpont et al., Anal. Bioanal. Chem., 373, 46-55 (2002); Ochiai, Gerstel Solutions Worldwide, 6, 17-19 (2006); Coleman, III, et al., J. Sci. Food and Agric., 84, 1223-1228 (2004); Coleman, III et al., J. Sci. Food and Agric., 85, 2645-2654 (2005); Pawliszyn, ed., Applications of Solid Phase Microextraction, RSC Chromatography Monographs, (Royal Society of Chemistry, UK) (1999); Sahraoui et al., J. Chrom., 1210, 229-233 (2008); and U.S. Pat. No. 5,301,694 to Raymond et al., which are all incorporated herein by reference.

Nicotine utilized according to the present disclosure can include nicotine in free base form, salt form, as a complex, or as a solvate. See, for example, the discussion of nicotine in free base form in US Pat. Pub. No. 2004/0191322 to Hansson, which is incorporated herein by reference. At least a portion of the nicotine can be employed in the form of a resin complex of nicotine where nicotine is bound in an ion exchange resin such as nicotine polacrilex. See, for example, U.S. Pat. No. 3,901,248 to Lichtneckert et al.; which is incorporated herein by reference. At least a portion of the nicotine can be employed in the form of a salt. Salts of nicotine can be provided using the types of ingredients and techniques set forth in U.S. Pat. No. 2,033,909 to Cox et al. and Perfetti, Beitrage Tabakforschung Int., 12, 43-54 (1983), the disclosures of which are incorporated herein by reference. Additionally, salts of nicotine have been available from sources such as Pfaltz and Bauer, Inc. and K&K Laboratories, Division of ICN Biochemicals, Inc. Exemplary pharmaceutically acceptable nicotine salts include nicotine salts of tartrate (e.g., nicotine tartrate and nicotine bitartrate) chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. In certain embodiments, at least a portion of the nicotine can be in the form of a salt with an organic acid moiety, including, but not limited to, levulinic acid as discussed in U.S. patent application Ser. No. 12/769,335 and International Application No. PCT/US2011/033928, both to Brinkley et al., which are incorporated herein by reference.

As used herein, a "flavorant" can refer to any material suitable for providing a sensory characteristic upon its release from the suspension. Exemplary sensory characteristics that can be modified by the flavor material include, taste, mouth feel, moistness, coolness/heat, and/or fragrance/aroma. In some embodiments, the flavorant specifically may exclude tobacco-derived materials.

The flavorant can be natural or synthetic, and the character of the flavorant can be described as, without limitation, fresh, sweet, herbal, confectionary, floral, fruity, spice, or combinations thereof. Non-limiting examples of flavorants that may be used include vanilla, coffee, tea, chocolate, cream, mint, spearmint, menthol, peppermint, wintergreen, lavender, cardamom, nutmeg, cinnamon, clove, cascarilla, sandalwood, honey, maple, jasmine, ginger, anise, sage, licorice, lemon, orange, apple, peach, lime, cherry, strawberry, and combinations thereof. Flavorants utilized in disclosed products also can include components that are considered moistening, cooling, or smoothening agents, such as eucalyptus. Flavorants may be provided neat (i.e., alone) or in a composite (e.g., spearmint and menthol, or orange and cinnamon). In some embodiments, the flavorant may be provided in a spray-dried form.

Flavorants can include sweeteners, which can be used in natural or artificial form or as a combination of artificial and natural sweeteners. In some embodiments, syrups (e.g. corn syrup), sucralose, sucrose, fructose, saccharin, acesulfame K, aspartame, isomalt, lactose, mannitol, sorbitol, xylitol, maltitol, or a combination thereof can be used as the primary sweetener ingredient.

For other examples of flavoring materials that may be suitable for use according to the present disclosure, see, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

As used herein, a "humectant" can refer to a material that is adapted to provide and/or retain moisture. A humectant particularly can be a hygroscopic material. A humectant can be a compound having one or more hydrophilic groups, particularly hydroxyl groups. Non-limiting examples of materials that may be utilized as humectants according to the present disclosure include polyols (e.g., glycerol, propylene glycol), triacetin (also known as glycerin triacetate or 1,2,3-triacetoxypropane), sugar alcohols (e.g., sorbitol, xylitol, maltitol), alpha hydroxy acids (e.g., lactic acid), honey, and combinations thereof.

As used herein, a "tobacco extract" can refer to a material that is derived from, but does not itself include, tobacco plant material, such as dried, shredded tobacco leaves. A tobacco extract can be an extract from any *Nicotiana* species. A tobacco extract may be provided in a liquid form and/or in a substantially solid form (e.g., pellet, particles, prills, flakes, beads, etc.). The *Nicotiana* species used to derive the extract can be selected for the content of various compounds that are present therein. For example, where tobacco extracts are employed in the articles of the present disclosure, plants can be selected on the basis that those plants produce relatively high quantities of one or more of the compounds desired to be isolated therefrom. In certain embodiments, plants of the *Nicotiana* species (e.g., Galpao commun tobacco) are specifically grown for their abundance of leaf surface compounds. Tobacco plants can be grown in greenhouses, growth chambers, or outdoors in fields, or grown hydroponically. The tobacco extract can include any component separated from, removed from, or derived from tobacco using tobacco extraction processing conditions and techniques. Purified extracts of tobacco or other botanicals specifically can be used. Typically, tobacco extracts are obtained using solvents, such as solvents having an aqueous nature (e.g., water) or organic solvents (e.g., alcohols, such as ethanol or alkanes, such as hexane). As such, extracted tobacco components are removed from tobacco and separated from the unextracted tobacco components; and for extracted tobacco components that are present within a solvent, (i) the solvent can be removed from the extracted tobacco components, or (ii) the mixture of extracted tobacco components and solvent can be used as such. Exemplary types of tobacco extracts, tobacco essences, solvents, tobacco extraction processing conditions and techniques, and tobacco extract collection and isolation procedures, are set forth in Australia Pat. No. 276,250 to Schachner; U.S. Pat. No. 2,805,669 to Meriro; U.S. Pat. No. 3,316,919 to Green et al.; U.S. Pat. No. 3,398,754 to Tughan; U.S. Pat. No. 3,424,171 to Rooker; U.S. Pat. No. 3,476,118 to Luttich; U.S. Pat. No. 4,150,677 to Osborne; U.S. Pat. No. 4,131,117 to Kite; U.S. Pat. No. 4,506,682 to Muller; U.S. Pat. No. 4,986,286 to Roberts et al.; U.S. Pat. No. 5,005,593 to Fagg; U.S. Pat. No. 5,065,775 to Fagg; U.S. Pat. No. 5,060,669 to White et al.; U.S. Pat. No. 5,074,319 to White et al.; U.S. Pat. No. 5,099,862 to White et al.; U.S. Pat. No. 5,121,757 to White et al.; U.S. Pat. No. 5,131,415 to Munoz et al.; U.S. Pat. No. 5,230,354 to Smith et al.; U.S. Pat. No. 5,235,992 to Sensabaugh; U.S. Pat. No. 5,243,999 to Smith; U.S. Pat. No. 5,301,694 to Raymond; U.S. Pat. No. 5,318,050 to Gonzalez-Parra et al.; U.S. Pat. No. 5,435,325 to Clapp et al.; and U.S. Pat. No. 5,445,169 to Brinkley et al.; the disclosures of which are incorporated herein by reference in their entireties.

The external phase material can be adapted to form a substantially wall-like structure that is pseudoplastic and is non-collapsible. The internal phase material (being substantially hydrophilic in nature) is substantially suspended within the external phase material, which is preferably substantially hydrophobic in nature. In particular, the external phase material can comprise a lipid. The external phase material can be a petroleum based and/or food based material, such as waxes, butters, oils, and the like. The external phase material preferably is a lipidic material having a melting point that is about 80° C. or greater, about 90° C. or greater, or about 100° C. or greater. In some embodiments, the melting point of the lipidic material can be about 90° C. to about 160° C. Non-limiting examples of lipidic materials that may be used in the external phase of a suspension according to the present disclosure include tallow, hydrogenated tallow, hydrogenated vegetable oil, almond oil, coconut oil, corn oil, cottonseed oil, light liquid petrolatum, heavy liquid petrolatum, olein, olive oil, palm oil, peanut oil, persic oil, sesame oil, soybean oil, and safflower oil. In some embodiments, stearines may be used in the external phase material. In some embodiments, the lipidic material particularly can comprise one or more hard butters—i.e., hydrogenated, press fractionated, or other processed oils that are processed or recombined to have a solid fat index (percent solid fat vs. temperature) similar to that of cocoa butter. Other materials suitable for use in the external phase material, as well as methods of forming suspensions suitable for use according to the present disclosure, are described in U.S. Pat. No. 6,340,471 and U.S. Pub. No. 2004/0096498, both to Kershman et al., both of which are incorporated herein by reference.

The internal phase of the suspension according to the present disclosure can be solid, liquid, or a combination thereof. In some embodiments, the internal phase particularly can be liquid such that the suspension can be characterized as being substantially a hydraulic encapsulation arising from a liquid-in-liquid microencapsulation process. In this manner, encapsulation of up to 98% by weight aqueous solution (based on the overall weight of the suspension) can be achieved while the suspension retains an overall hydrophobic nature relative to the external environment due to the lipidic characteristics of the wall structure. Accordingly, the suspension itself can be incorporated into a solution, if desired, under which conditions the suspension is substantially in the form of aggregates of individual microcapsules surrounded with a continuous lamellae. Because of this structure, the suspension can be substantially bioadhesive. In this sense, bioadhesion is understood to mean a state in which two materials, at least one of which is biological in nature, are held together for extended periods of time by interfacial forces. The suspension according to the present disclosure can be bioadhesive in that it is adapted for attachment (without the requirement of an additional adhesive element) to human or animal tissue. In particular, the presently disclosed suspension can be adapted for bioadhesion to epithelial tissue and/or to the mucus coating on the surface of a tissue (i.e., mucoadhesion). In particular embodiments, the present suspension can be adapted for bioadhesion (or mucoadhesion specifically) to oral, nasal, and/or esophageal tissue.

In various embodiments, the suspension can comprise about 50% by weight to about 98% by weight, about 60% by weight to about 98% by weight, or about 75% to about 98% by weight of the internal phase material. In other embodiments, the suspension can comprise about 1% by weight to about 98% by weight, about 5% by weight to about 95% by weight, or about 10% by weight to about 90% by weight of the internal phase material.

As noted above, the combination of the internal phase and the external phase may be characterized as being a "hydraulic encapsulation" or a "hydraulic suspension." By such is meant that a liquid internal phase material is confined within the external phase material such that there is a pressure differential between the internal phase liquid and the external environment. Accordingly, release of the internal phase material can be driven through osmotic pressure differentials in particular between the internal phase and the external phase. It is thus possible according to the present disclosure to tune the release of the internal phase material based on its osmotic concentration. Release can be configured to be substantially immediate upon delivery of the suspension or can be delayed and/or sustained. Substantially immediate delivery can mean release of at least 50% by weight of the internal phase material within a time of about 5 seconds to about 60 seconds after delivery of the suspension. Sustained release can mean a substantially continuous release of the internal phase material for a time of at least 5 minutes, at least 10 minutes, at least 30 minutes, at least 1 hr, at least 2 hrs, at least 6 hrs, at least 12 hrs, or at least 24 hrs after delivery of the suspension. Delayed release can mean that no more than about 10% by weight of the internal phase material is released until about 10 minutes, about 30 minutes, about 1 hr, about 2 hrs, about 6 hrs, or about 12 hrs after delivery of the suspension.

If desired, release can be facilitated through inclusion of one or more expansible materials within the external phase. An expansible material, for example, may be a hydrophilic material that is adapted for uptake of fluid (e.g., saliva when delivered orally) that causes significant expansion of the material. Since the external phase material can form a semi-permeable membrane, expanding fluid may pass therethrough for uptake by the expansible material. The expansion can cause or assist in causing rupturing of the external phase and release of the internal phase material. Examples of expansible materials include but are not limited to polysaccharides, starches and carbohydrates. In a preferred embodiment, the swellable material can be carboxymethyl cellulose, hydroxypropyl cellulose, hydroxypropyl methyl cellulose, methyl cellulose, high-molecular weight polyethylene glycol, high-molecular weight propylene glycol, gelatin, docusate, sodium alginate, sodium starch glycolate, sorbitol, and high molecular weight sugars. Such materials can be useful to facilitate release of the internal phase material through changes in the osmotic pressure differential of the suspension. Materials and methods for membrane rupturing through use of swellable materials and/or materials suitable for altering osmotic pressure are described in U.S. Pat. No. 6,312,731 to Staas et al., which is incorporated herein by reference.

In some embodiments, the internal phase material can be released at a rate of about 0.25% by weight per minute to about 5% by weight per minute, about 0.25% by weight per minute to about 3% by weight per minute, or about 0.5% by weight per minute to about 1.5% by weight per minute. The release can be substantially constant or can vary within the noted ranges.

The suspension according to the present disclosure can be characterized in some embodiments in that the suspension remains stable for an extended period of time. Stability can mean that the release rate of the internal phase material after storage can be substantially the same as the release rate of the internal phase material immediately after formation of the suspension. Storage conditions can be substantially ambient temperature and humidity. In some embodiments, the suspension can be stable in that after storage for a time of up to one year, and the release rate changes by about no more than 20%. In other embodiments, the suspension can remain stable in that, after a storage time of up to six months, the release rate changes by about no more than 10%. In further embodiments, the suspension can remain stable in that, after a storage time of up to three months, and the release rate changes by about no more than 5%.

The internal phase material may, in some embodiments, be encapsulated within an encapsulating layer when combined with a lipidic material to form the suspension. As such, the internal phase material can be characterized as being pre-encapsulated. Encapsulation of the internal phase material can be carried out using any suitable technique. For example, microcapsules can be formed using any of various chemical encapsulation techniques such as solvent evaporation, solvent extraction, organic phase separation, interfacial polymerization, simple and complex coacervation, in-situ polymerization, liposome encapsulation, and nanoencapsulation. Alternatively, physical methods of encapsulation could be used, such as spray coating, pan coating, fluid bed coating, annular jet coating, spinning disk atomization, spray cooling, spray drying, spray chilling, stationary nozzle coextrusion, centrifugal head coextrusion, or submerged nozzle coextrusion.

Regardless of the encapsulation methodology employed, the outer wall or shell material and solvents used to form the capsules can vary. Classes of materials that are typically used as wall or shell materials include proteins, polysaccharides, starches, waxes, fats, natural and synthetic polymers, and resins. Exemplary materials for use in the microencapsulation process used to form the microcapsules include gelatin, acacia (gum arabic), polyvinyl acetate, potassium alginate, carob bean gum, potassium citrate, carrageenan, potassium polymetaphosphate, citric acid, potassium tripolyphosphate, dextrin, polyvinyl alcohol, povidone, dimethylpolysiloxane, dimethyl silicone, refined paraffin wax, ethylcellulose, bleached shellac, modified food starch, sodium alginate, guar gum, sodium, sodium citrate, carboxymethylcellulose, hydroxypropyl cellulose, hydroxypropylmethylcellulose, sodium ferrocyanide, sodium polyphosphates, locust bean gum, methylcellulose, sodium trimetaphosphate, methyl ethyl cellulose, sodium tripolyphosphate, microcrystalline wax, tannic acid, petroleum wax, terpene resin, tragacanth, polyethylene, xanthan gum, and polyethylene glycol.

Microcapsules are commercially available, and exemplary types of microcapsule technologies are of the type set forth in Gutcho, Microcapsules and Microencapsulation Techniques (1976); Gutcho, Microcapsules and Other Capsules Advances Since 1975 (1979); Kondo, Microcapsule Processing and Technology (1979); Iwamoto et al., AAPS Pharm. Sci. Tech. 2002 3(3): article 25; U.S. Pat. No. 5,004,595 to Cherukuri et al.; U.S. Pat. No. 5,690,990 to Bonner; U.S. Pat. No. 5,759,599 to Wampler et al.; U.S. Pat. No. 6,039,901 to Soper et al.; U.S. Pat. No. 6,045,835 to Soper et al.; U.S. Pat. No. 6,056,992 to Lew; U.S. Pat. No. 6,106,875 to Soper et al.; U.S. Pat. No. 6,117,455 to Takada et al.; U.S. Pat. No. 6,482,433 to DeRoos et al.; and U.S. Pat. No. 6,929,814 to Bouwmeesters et al.; each of which is incorporated herein by reference.

In some embodiments, the suspension can be combined with a carrier. The carrier can be a solid material or can be a liquid material. For example, the suspension can be substantially coated on a solid carrier. In some embodiments, where a porous carrier may be used, the suspension can be substantially absorbed within pores of the solid carrier. A solid carrier can be dissolvable under mouth conditions. The term mouth conditions can encompass one or more characteristics (in any combination) associated with the presence of an item in the mouth of a user. For example, mouth conditions can include any combination of temperature, moisture, and pH typically found in the mouth of a human as well as the shear, compression, and other mechanical forces that may be applied by the teeth during chewing. Mouth conditions particularly can relate to being in contact with saliva. Mouth conditions can include conditions wherein a material is solubilized in a solvent that is substantially similar to saliva. For example, in some embodiments, mouth conditions can relate to being in contact with an aqueous solvent.

A solid carrier for use according to the present disclosure can include a wide variety of materials that are suitable human or animal use. For example, a carrier can be a lozenge, tablet, pastille, or like unit that is configured for oral use. Compositions suitable for use as an oral carrier according to the present disclosure, and methods of manufacture thereof, are described, for example, in U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al. and U.S. Pat. No. 6,248,760 to Wilhelmsen; U.S. Pat. No. 8,741,348 to Hansson et al., US Pat. Pub. No. 2001/0016593 to Wilhelmsen, US Pat. Pub. No. 2010/0004294 to Axelsson et al., and US Pat. Pub. No. 2013/0209540 to Duggins et al., all of which are incorporated herein by reference.

In some embodiments, a solid carrier can be substantially in the form of a thin film or strip. As further described herein, thin films or strips can comprise a single layer or a plurality of layers and may have an active ingredient (such as a suspension according to the present disclosure) substantially coated on the thin film, dispersed throughout at least a portion of the thin film, absorbed in or adsorbed on the thin film, and/or sandwiched between two or more thin films. For example, in some embodiments, a composition according to the present disclosure can be a layered construct comprising a first thin film, a second thin film, and a suspension as described herein that is positioned between the first thin and the second thin film.

Materials for forming thin films can be substantially dissolvable under mouth conditions and may be configured for rapid dissolution, delayed dissolution, and/or sustained dissolution over an extended period of time. In some embodiments, a plurality of thin films may be combined wherein one thin film has a first dissolution profile and a second thin film has a second dissolution profile that is different from the first dissolution profile. For example, under the same conditions, one of the first thin film and the second thin film can be configured to dissolve at a rate that is faster than the other by a rate of about 10% or greater, about 20% or greater, or about 50% or greater (e.g., greater by about 10% to about 500%, about 20% to about 250%, or about 30% to about 200%). In some embodiments, one of the first thin film and the second thin film can be dissolvable under mouth conditions, and the other thin film can be substantially non-dissolvable under mouth conditions. Compositions suitable for use as thin film carrier according to the present disclosure, and methods of manufacture thereof, are described, for example, in U.S. Pat. No. 5,948,430 to Zerbe, U.S. Pat. No. 6,072,100 to Mooney et al., U.S. Pat. No. 6,375,963 to Repka et al., U.S. Pat. No. 6,596,298 to Leung et al., U.S. Pat. No. 6,709,671 to Zerbe et al., U.S. Pat. No. 6,923,981 to Leung et al., U.S. Pat. No. 7,025,983 to Leung et al., U.S. Pat. No. 7,491,406 to Leung et al., U.S. Pat. No. RE33,093 to Schiraldi et al., U.S. Pat. Pub. Nos. 2003/0107149 and 2005/0037055 to Yang et al., US Pat. Pub. No. 2006/0198873 to Chan et al., US Pat. Pub. No. 2006/0204559 to Bess et al., U.S. Pat. Pub. No. 2007/0202057 to Frankhauser et al., and U.S. Pat. Pub. No. 2009/0095313 to Fuisz, all of which are incorporated herein by reference.

In further embodiments, a solid carrier can be in the form of a gum whereby a suspension material as described herein may be released therefrom during chewing of the gum base. Compositions suitable for use as gum carrier according to the present disclosure, and methods of manufacture thereof, are described, for example, in U.S. Pat. No. 3,845,217 to Ferno et al., U.S. Pat. No. 3,877,468 to Lichtneckert et al., U.S. Pat. No. 3,901,248 to Lichtneckert et al., U.S. Pat. No. 6,344,222 to Cherukuri et al, U.S. Pat. No. 6,358,060 to Pinney et al., U.S. Pat. No. 6,773,716 to Ream et al., U.S. Pat. No. 6,893,654 to Pinney et al., and U.S. Pat. Pub. No. 2004/0191322 to Hansson, all of which are incorporated herein by reference.

In some embodiments, a solid carrier for a suspension as described herein can be a natural tobacco material. The tobacco material can be substantially in any solid form that is known to be suitable for use such as, for example, dissolvable tobacco products (e.g., fine powdered tobacco compressed or otherwise formed into solid units, such as strips, sticks, orbs, and lozenges), chewing tobacco (e.g., in a loose leaf, plug, or twist form), dry snuff, moist snuff, pouches (i.e., fine tobacco contained within a sachet or fleece), and snus.

Natural tobacco as used herein can mean some form of a plant of the *Nicotiana* species. The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). Additional information on types of *Nicotiana* species suitable for use in the present invention can be found in US Pat. Appl. Pub. No. 2012/0192880 to Dube et al., which is incorporated by reference herein. Tobacco plants can be grown in greenhouses, growth chambers, or outdoors in fields, or grown hydroponically.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material may thus comprise an entire plant or any portion of a plant of the *Nicotiana* species. See, for example, the portions of tobacco plants set forth in US Pat. Appl. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green form or a cured form, as described in 2012/0192880 to Dube et al., which is incorporated by reference herein.

The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching, or otherwise subjected to storage or treatment for later use. Exemplary processing techniques are described, for example, in US Pat. Appl. Pub. Nos. 2009/0025739 to Brinkley et al. and 2011/0174323 to Coleman, III et al., which are incorporated by reference herein.

Tobacco materials can be treated with enzymes and/or probiotics before or after harvest, as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference. Tobacco materials may be irradiated, pasteurized, or otherwise subjected to controlled heat treatment. Representative processes are set forth in US Pat. Pub. Nos. 2009/0025738 to Mua et al.; 2009/0025739 to Brinkley et al.; and 2011/0247640 to Beeson et al., which are incorporated herein by reference. The tobacco material can be brought into contact with an imprinted polymer or non-imprinted polymer such as described, for example, in US Pat. Pub. Nos. 2007/0186940 to Bhattacharyya et al; 2011/0041859 to Rees et al.; 2011/0159160 to Jonsson et al; and 2012/0291793 to Byrd et al., all of which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant.

In certain embodiments, the tobacco material is used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size less than about 50 microns. In one embodiment, the average particle size of the tobacco particles may be less than or equal to about 25 microns. In some instances, the tobacco particles may be sized to pass through a screen mesh. If desired, air classification equipment may be used to ensure that small sized tobacco particles of the desired sizes, or range of sizes, may be collected. If desired, differently sized pieces of granulated tobacco may be mixed together. Use of micro-milled tobacco particles (or other micro-sized botanical components) can be advantageous where the user prefers to reduce or eliminate product waste after use.

A solid carrier can, in some embodiments, comprise one or more materials suitable for use as a tobacco substitute. As used herein, a tobacco substitute can be any material that can be provided in a form that is substantially similar to a form of tobacco, such as shreds, powders, and the like, and that is suitable as a carrier for the suspension as described herein. For example, in some embodiments, a tobacco substitute can include calcium polycarbophil, microcrystalline cellulose, cornstarch, beet pulp fiber, silicon dioxide, calcium carbonate, and combinations thereof.

In some embodiments, a solid carrier can include a fabric, which may be in the form of a pouch (which may also be referred to as a fleece). In such form, a suspension as described herein may be carried by the fabric and/or carried by a further material (e.g., a tobacco material and/or a tobacco substitute) included within the pouch form of the fabric. A pouch preferably can be moisture-permeable. For example, suitable packets, pouches, or containers of the type used for the manufacture of smokeless tobacco products that can be suitable for use according to the present disclosure are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf, and TreAnkrare. A pouch type of product similar in shape and form to various embodiments of a pouched product that may be useful according to the present disclosure is commercially available as ZONNIC (distributed by Niconovum AB). Additionally, pouch type products generally similar in shape and form to embodiments useful according to the present disclosure are set forth as snuff bag compositions E through J in Example 1 of PCT WO 2007/104573 to Axelsson et al., which is incorporated herein by reference, which are produced using excipient ingredients and processing conditions that can be used to manufacture pouched products as described herein.

A water-permeable fabric useful as a pouch to house a composition comprising a carrier and a suspension as described herein can comprise a nonwoven web. During use, a user can place one pouched product containing the composition in the mouth of the human subject/user. The mouth conditions, particularly contact with saliva, cause at least a portion of the suspension to be released from the composition and/or can cause at least a portion of the internal phase material to be released from the suspension. The pouch preferably is not swallowed. The pouch may be subject to chewing but is preferably not chewed so as to substantially tear or otherwise perforate the pouch and allow the composition to spill into the mouth. After a suitable time (e.g., about 30 seconds to about 60 minutes, about 1 minutes to about 45 minutes, or about 2 minutes to about 30 minutes), the pouch may be removed from the mouth of the human subject for disposal.

The pouch can be formed of any material that is suitable for use in the human mouth and that is sufficiently moisture-permeable, liquid-permeable, and/or water-permeable so as to allow for movement of the releasable components from the composition contained therein, particularly when in contact with saliva. As used herein, the term "water-permeable" particularly includes saliva-permeable.

The pouch material may be of a type that may be considered to be similar in character to the mesh-like type of material that is used for the construction of a tea bag. The suspension and/or the internal phase material of the suspension can readily diffuse through the pouch and into the mouth of the user (or into a surrounding environment, such as the fluid into which a pouched product may be placed, for example in embodiments wherein the pouched product may be a tea bag or the like). Preferred fabric materials for a pouch may be designed and manufactured such that under conditions of normal use, a significant amount of the suspension and/or the internal phase material can permeate through the pouch prior to the time that the pouch undergoes loss of its physical integrity.

In other embodiments, the suspension can be in admixture with a liquid carrier. Such liquid carrier may be substantially hydrophilic or substantially hydrophobic in nature. In some embodiments, an emulsifier or other additives useful for providing a substantially homogeneous mixture of the suspension within the liquid carrier may be included.

A composition wherein the suspension is provided in a liquid carrier can be adapted particularly for use as a spray, such as a nasal spray, oral spray, or the like. Various exemplary ways to administer nicotine in the form of a nasal spray are set forth in U.S. Pat. No. 4,579,858 to Ferno et al.; U.S. Pat. No. 5,656,255 to Jones and U.S. Pat. No. 6,596,740 to Jones, which are incorporated herein by reference. Various exemplary ways to administer nicotine in the form of an oral spray (i.e., suitable for buccal administration), are set forth in U.S. Pat. No. 6,024,097 to Von Wielligh; U.S. Pat. Pub. No. 2003/0159702 to Lindell et al.; U.S. Pat. Pub. No. 2007/0163610 to Lindell et al., U.S. Pat. Pub. No. 2009/0023819 to Axelsson, EP 1458388 to Lindell et al., and PCT Pat. Pub. No. WO 2008/037470 to Axelsson et al., all of which are incorporated herein by reference.

Compositions as described herein can be useful in formation of a wide variety of products. In particular, the compositions may be useful in any product where it is desirable to provide for delivery of one or more of nicotine, flavorants, humectants, and tobacco extracts.

In some embodiments, the compositions described herein can be suitable for use in nicotine replacement therapy products. As such, the suspension can comprise nicotine as the internal phase material. Additional materials may be included in the same suspension. Alternatively, a first suspension may be included in the product, the first suspension comprising nicotine as the internal phase material, and a second suspension may be included in the product, the second suspension comprising one or more further materials (e.g., flavorants, humectants, or tobacco extracts) as the internal phase material.

In some aspects, the present disclosure can relate to an oral strip. In some embodiments, an oral strip can comprise a thin film and a suspension as otherwise described herein carried by the thin film. In particular, the suspension can comprise an external phase formed of a lipid and an internal phase that includes a material selected from the group consisting of nicotine, flavorants, humectants, tobacco extracts, and combinations thereof.

An exemplary embodiment of a strip according to the present disclosure is shown in FIG. 1. As seen therein, the strip 100 is formed of a thin film 120 and a suspension 130 carried thereby. In the illustrated embodiment, the suspension is coated onto the thin film. In other embodiments, the suspension can be substantially dispersed in the thin film.

A strip can comprise a plurality of thin films, as illustrated in FIG. 2. As seen therein, a first thin film 220 and second thin film 225 are combined to form the strip 200. The suspension 230 is applied to the first thin film 220 so as to be positioned between the first thin and the second thin film 225. Alternatively, the suspension 230 may be applied to the second thin film 225, applied to both of the first thin film 220 and the second thin film, or physically entrapped between the thin films, including being positioned within a cavity or well that is formed in one or both of the thin films. In such configuration, both of the first thin film 220 and the second thin film 225 can be substantially dissolvable under mouth conditions so as to release the suspension 230. In preferred embodiments, the suspension 230 can be configured for bioadhesion such that, upon release of the suspension, the material may substantially adhere to at least a portion of the tissue in the oral cavity so that the internal phase material can be released from the external phase. In some embodiments, as a non-limiting example, the first thin film 220 can be substantially non-dissolvable under mouth conditions or can be slowly dissolving relative to the second thin film 225, which can be configured to dissolve rapidly or more rapidly than the first thin film. The first thin film 220 and the second thin film 225 may be distinguishable (e.g., a different color, different texture, or the like) so that a consumer can insert the strip 200 into the oral cavity so that the second thin film 225 can be in direct contact with the oral tissue such that the second thin film can dissolve to release the suspension 230 while the first thin film 220 remains substantially intact for at least a minimum amount of time to maintain the suspension at the delivery site and substantially prevent loss of the suspension, such as by swallowing. It is understood that the relative dissolvabilities of the first thin film and second thin film may be reversed in such embodiments. More than two thin films may be combined. For example, three thin films may be stacked with suspension between the bottom and middle layers and between the middle and top layers. The same suspension may be used in each location or different suspensions can be used. Moreover, the thin films may be configured for relative dissolvability such that one of the suspensions can be released before the other suspension. In this manner, a variety of effects and sensations can be provided with a timed release.

In some aspects, the present disclosure can relate to a spray system. The spray system can be configured for housing and spraying of a liquid composition. While the word "spray" is used, it is understood that delivery of the liquid can take on any form wherein the liquid is delivered from the system, such as providing a stream, droplets, a mist, or the like. It is further understood that a "spray" system encompasses systems wherein the liquid is delivered by spraying (e.g., with the use of an added propellant or the like) as well as by pumping or any similar manner wherein the liquid is delivered from a container by mechanical means. Thus, at a minimum, the present system can be characterized as a spray system, a pump system, or a liquid delivery system.

An exemplary embodiment of a spray delivery system 300 according to the present disclosure is shown in FIG. 3. As seen therein, a spray delivery system 300 can comprise a container 310 configured for containing a liquid. In the illustrated embodiment, the container is partially cut away to reveal the liquid therein. In particular, a sprayable liquid carrier 315 is included in the container, and a suspension 330 is intermixed with the sprayable liquid carrier. In use, a consumer can direct the spray nozzle 312 of the container 310 to the delivery location (e.g., into the oral cavity) and actuate the nozzle to spray the suspension intermixed with the sprayable liquid carrier. Further examples of containers configured for delivery of a spray composition or other liquid composition are described in U.S. Pat. Pub. No. 2010/0108059 to Axelsson et al., which is incorporated herein by reference.

In some aspects, the present disclosure can relate to a smokeless tobacco product. In particular, a smokeless tobacco material can have a dressing material combined therewith, and the dressing material can comprise a suspension as described herein. For example, the smokeless tobacco material may comprise solid tobacco in any form typically recognized for oral use. An exemplary embodiment of a smokeless tobacco product 400 is a shown in FIG. 4, wherein a smokeless tobacco material 440 is retained within a fabric pouch 445. A suspension according to the present disclosure can be carried by one or both of the smokeless tobacco material 440 and the fabric pouch 400. When carried by both, different suspensions may be used on the smokeless tobacco material and the fabric pouch (or the same suspension may be used with both).

As a non-limiting example, a smokeless tobacco material in the form of a fine powder may commonly be referred to as snus, and the material may be provided free within a canister or other packaging or may be provided within a pouch (such as shown in FIG. 4). While snus is typically substantially dry, in some embodiments, a suspension as presently disclosed may particularly include humectants or tobacco derived extracts as the internal phase. The addition of the humectant or tobacco derived extract can allow the typically dry, fine tobacco to appear substantially similar to a moist snuff. To this end, nicotine, flavorants, and/or selectively filtered tobacco extracts likewise can be provided in as the internal phase of a suspension.

In some embodiments, the smokeless tobacco material can include or be replaced with a smokeless tobacco substitute. Any material suitable to provide a look, feel, and/or texture of a natural tobacco material can be used as the tobacco substitute. As desired, the suspension carried by the smokeless tobacco substitute can include internal phase materials suitable to achieve substantially the same appearance, perception, and/or sensations as a natural tobacco material.

In some aspects, the present disclosure can relate to an aerosol delivery device. Such devices are generally known in the art, and the present disclosure can be applied to any of such devices which purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators, and medicinal inhalers that are configured to vaporize or heat a volatile material, or attempt to provide the sensations of cigarette, cigar or pipe smoking without burning tobacco to a significant degree. An aerosol delivery device as described herein can include devices that are electrically powered, so-called "e-cigarettes" as well as devices that are heated by a fuel element or the like, such as so-called "heat-not-burn" devices. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Non-limiting examples of various types of electrically powered aerosol and vapor delivery devices, the materials and components useful in forming such devices, methods of making such devices, and methods of aerosol generation utilizing such devices are described in U.S. Pat. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference. Materials and components useful in forming heat-not-burn devices are described in U.S. Pat. No. 4,989,619 to Clearman et al., U.S. Pat. No. 5,137,034 to Perfetti et al., U.S. Pat. No. 5,178,167 to Riggs et al., U.S. Pat. No. 5,345,955, to Clearman et al., U.S. Pat. No. 5,551,451 to Riggs et al., U.S. Pat. No. 5,593,792 to Farrier et al., U.S. Pat. No. 6,095,152 to Beven et al. U.S. Pat. No. 7,647,932 to Cantrell et al., which are incorporated herein by reference.

An exemplary embodiment of an aerosol delivery device 500 is shown in FIG. 5. As seen therein, the aerosol delivery device comprises a housing 550 with an air inlet 551 and a mouthend 552 positioned downstream from the air inlet and including an aerosol outlet 553. A heat source 565 is positioned upstream from the mouth end 552 of the device. A reservoir 560 is likewise positioned upstream from the mouth end 552 of the device and is configured for holding an aerosol precursor composition. As illustrated, the reservoir 560 is positioned upstream from the heat source 565; however, it is understood that the heat source may be positioned upstream from the reservoir. In some embodiments, the reservoir 560 may be a fibrous material or may be substantially configured as a container. In some embodiments, the reservoir 560 may be a tobacco material that may have an aerosol forming material combined therewith. In some embodiments, the heat source 565 can be an electric heater. In some embodiments, the heat source 565 can be a fuel element. In FIG. 5, at least one liquid transport element 563 extends between the reservoir 560 and the heat source 565, although such liquid transport elements may be absent in some embodiments, such as where the heat source is in sufficient proximity to the reservoir to at least partially vaporize any aerosol precursor composition stored therein. The aerosol delivery device 500 is configured so that an air flow stream 557 passes at least partially through the housing 550. Preferably, the air flow stream 557 at least passes between the heat source and the mouth end 552 of the device. As illustrated, the airflow stream 557 enters at the air inlet 551, passes around and/or through the reservoir 560, passes across the heat source 565, and proceeds to the mouth end 552 of the device. In use, the heat source 565 functions to vaporize aerosol precursor composition held in the reservoir 560 such that the vapor mixes with air in the air flow stream 557 to form an inhalable aerosol, which exits the device through the aerosol outlet 553. If desired, the air inlet 551 may be positioned elsewhere on the housing 550. The aerosol delivery device 500 further includes a carrier element 567 positioned in the air flow stream 557 between the heat source 565 and the mouth end 552 of the device. The carrier element 567 can be any material suitable for retaining a suspension as otherwise described herein in a manner such that at least a portion of the suspension and/or the internal phase material held in the suspension may be entrained by aerosol passing through the air flow stream 557. For example, the carrier may be a fabric, fibers, particles, beads, ceramics, and the like.

In embodiments related to an aerosol delivery device, an aerosol precursor composition used therein may be devoid of any flavors and/or nicotine. Rather, the aerosol precursor composition may consist essentially of a humectant, such as a polyol, so as to be substantially plain, or generic. Desired flavors and/or nicotine may be provided in the suspension (along with additional humectants and/or tobacco extracts, if desired).

In some aspects, the present disclosure can relate to packaging. For example, it can be desirable for packaging for various types of products to be configured for release of various materials therein. For example, a suspension as described herein can be provided with packaging wherein a flavorant or aroma material can used as the internal phase of the suspension. The internal phase may be configured for release through the external phase to provide flavor to a product within the packaging and/or to provide a desired aroma to the product. Likewise, a humectant may be provided as the internal phase of the suspension so as to control the moisture level within the package and/or to provide moisture to the product in the package.

In some embodiments, the present disclosure can relate to packaging for a tobacco product. The packaging can be a walled container, such as: a cigarette pack or carton; a smokeless tobacco canister, puck, or tin; a package for holding an aerosol delivery device; or similar packaging. The suspension can be present within the package. For example, the suspension can be coated onto an inner surface of at least one wall of a container. The suspension can be provided on or in a carrier that is provided within the container (e.g., a pouch or fleece holding the suspension, which may be coated or otherwise provided on particles, fibers, or the like that are held within the pouch). See, for example, U.S. Pat. No. 5,249,676 to Ashcraft et al., which is incorporated herein by reference.

An embodiment of a cigarette package according to the present disclosure is shown in FIG. 6. As seen therein, the cigarette package 600 comprises a body 671 and a lid 673 hinged to the body. The body comprises a front wall 671*a*, a back wall 671*b*, a first side wall 671*c*, a second side wall 671*d*, and a bottom wall 671*e*. Each of the respective walls has an inner surface and an outer surface. As illustrated, a suspension 630 according to the present disclosure is provided on a portion of the inner surface of the back wall 671*b*. It is understood that the suspension 630 may be present on one wall or a plurality of walls and/or may be present on an inner surface of the lid 673. The suspension can be provided within a pouch similar to the pouch illustrated in FIG. 4. Such pouch can include a carrier on which the suspension is provided. A cigarette package that can include a suspension as described herein can have a structure, for example, that is substantially as described in, for example, U.S. Pat. No. 4,895,251 to Focke et al., U.S. Pat. No. 4,949,841 to Focke, U.S. Pat. No. 6,276,600 to Rigby, U.S. Pat. No. 7,455,176 to Focke et al., and U.S. Pat. No. D651,073 to Cadieux, Jr. et al., which are incorporated herein by reference.

An embodiment of a smokeless tobacco container according to the present disclosure is shown in FIG. 7. As seen therein, the container 700 comprises a container lid 780 and a container body 785. The container lid 780 is formed of a lid wall 781 and skirt 783. The container body 785 is formed of a base wall 786, a first circumferential wall 787 attached to the base wall, and a second circumferential wall 788 attached to the first circumferential wall and inset therefrom. The container lid 780 is configured to engage the container body 785 such that the lid skirt 783 slides over the second circumferential wall 788. As illustrated, a suspension 730 according to the present disclosure is provided on a portion of an inner surface of the first circumferential wall 787. It is understood that the suspension may be present on one wall or a plurality of walls and/or may be present on an inner surface of the container lid 780. The suspension can be provided within a pouch similar to the pouch illustrated in FIG. 4. Such pouch can include a carrier on which the suspension is provided. If desired, such pouch may be substantially adhered to the container body 785 or a portion thereof or to the container lid 780 or a portion thereof. A container for smokeless tobacco products that can include a suspension as described herein can have a structure that is substantially as described, for example, in U.S. Pat. No. 8,910,781 to Pipes et al., U.S. Pat. No. D694,102 to Bellamah et al., U.S. Pat. Pub. No. 2011/0303566 to Gibson et al., U.S. Pat. Pub. No. 2012/0168329 to Berggren, U.S. Pat. Pub. No. 2012/0193265 to Patel et al., and U.S. Pat. Pub. No. 2012/0285125 to Baily et al., which are incorporated herein by reference.

In some aspects, the present disclosure can relate to a conventional smoking article—i.e., a cigarette, cigar, or the like. The smoking article can comprise a tobacco rod, a filter element connected to the tobacco rod, and a suspension as otherwise described herein. The suspension can be incorporated into the tobacco rod, the filter element, or both. For example, the suspension may be applied to the tobacco material used in the tobacco rod. In some embodiments, the suspension may be provided in a breakable capsule that may inserted, for example, into the filter element. The capsule may be ruptured when desired to release the suspension into the filter to be substantially entrained into the smoke passing therethrough. Exemplary materials that may be utilized in forming a smoking article are described in U.S. Pat. No. 7,565,818 to Thomas et al., U.S. Pat. No. 7,793,665 to Dube et al., and U.S. Pat. No. 8,512,213 to Deal, which are incorporated herein by reference. Various representative tobacco types, processed types of tobaccos, types of tobacco blends, smoking article components, and smoking article configurations that may be incorporated into a smoking article of the present disclosure are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; U.S. Pat. No. 7,017,585 to Li et al.; U.S. Pat. No. 7,025,066 to Lawson et al.; U.S. Pat. Pub. No. 2004-0255965 to Perfetti et al.; PCT WO 02/37990 to Bereman; and Bombick et al., Fund. Appl. Toxicol., 39, p. 11-17 (1997); which are incorporated herein by reference.

An exemplary embodiment of a cigarette according to the present disclosure is shown in FIG. 8. In particular, the cigarette 800 comprises a tobacco rod 890 and a filter 895. In the illustrated embodiment, a suspension 897 is provided on an outer surface of the filter 895. In other embodiments, the suspension may be incorporated into the tobacco rod 890 and/or into an internal portion of the filter 895, and/or into a wrapping paper or tipping paper (both of which are not shown in FIG. 8). In some embodiments, the suspension may be incorporated into a breakable capsule (the capsule 890 being shown in FIG. 8 as being positionable within the filter 895. Methods of manufacturing filter elements having a breakable capsule therein are described in U.S. Pat. No. 7,836,895 to Dube et al., which is incorporated herein by reference.

In some embodiments, a suspension can substantially form a band or a plurality of bands around a portion of the tobacco rod and/or around at least a portion of the filter of the cigarette. For example, Fire Standard Compliant (FSC) cigarettes are known to include one or more bands formed of additional wrapping paper and/or polymeric materials that function to slow burning so that an unattended cigarette will self-extinguish. A suspension as described herein similarly may be banded around a cigarette. In some embodiments, a suspension as described herein can be combined with an FSC band. The suspension can include internal phase materials that can enhance flavor. In some embodiments, a band of a suspension as described herein may be used alone to form an FSC band. If desired, the suspension may include materials (e.g., water and/or humectants) in the internal phase that can function to extinguish the cigarette if left unattended.

Examples

To evaluate the ability of the compositions of the invention to provide storage stable nicotine delivery products, dissolution tests were carried out on four different formulations that consisted of two different external phase materials (labeled 59-80A and 59-87B) suspending nicotine at a concentration of 0.8% by weight or 1.6% by weight, based on the total weight of the composition.

To evaluate nicotine release, 50 mg of the composition (i.e., the external phase material combined with the nicotine internal phase material) was dissolved in 5 mL of heptane. After mixing, 5 mL of deionized water (pH 3.0) was added. The solution was subjected to LC-UV testing. The dissolution testing illustrated release of the nicotine from the suspension, and storage stability was also evaluated by carrying out a first set of tests approximately 24 hours after preparation of the formulations and carrying out a second set of tests approximately 3 months after preparation during which time the formulations were stored at room temperature and humidity. The graph of FIG. 9 shows test results for the 0.8% by weight nicotine suspensions, and the graph of FIG. 10 shows the test results for the 1.6% by weight nicotine suspensions (each with an approximate 10% margin of error). As seen in the graphs (wherein 1 on the X axis indicates 100% release), the release rate curves for 0.8% by weight nicotine and 1.6% by weight nicotine are substantially similar. Likewise, the release rates of each formulation remained substantially similar after 3 months of storage.

It will be readily apparent to one of ordinary skill in the relevant arts that suitable modifications and adaptations to the compositions, methods, processes, and applications described herein can be made without departing from the scope of any embodiments or aspects thereof. Having now described the various embodiments and aspects of the claimed inventions in detail, the same will be more clearly understood by reference to the following examples, which are included herewith for purposes of illustration only and are not intended to be limiting. The scope of the disclosure provided herein includes all actual or potential combinations of embodiments, aspects, examples, and preferences herein described. All patents and publications cited herein are incorporated by reference herein for the specific teachings thereof.

The invention claimed is:

1. A delivery composition comprising:
    (a) a carrier; and
    (b) an aggregate of microcapsules each formed of an external phase surrounding an internal phase as a hydraulic encapsulation such that there is a pressure differential between the internal phase and an external environment at a site of delivery;
    wherein the internal phase is hydrophilic and comprises a material selected from the group consisting of nicotine, flavorants, humectants, tobacco extracts, water, and combinations thereof; and
    wherein the external phase is hydrophobic, comprises a lipid, and forms a substantially wall-like structure that is pseudoplastic and is non-collapsible.

2. The composition of claim 1, wherein the internal phase material is a liquid.

3. The composition of claim 1, wherein the aggregate of microcapsules is bioadhesive.

4. The composition of claim 1, wherein the carrier is a solid.

5. The composition of claim 4, wherein the solid carrier is dissolvable under mouth conditions.

6. The composition of claim 4, wherein the solid carrier is a gum or a lozenge.

7. The composition of claim 4, wherein the solid carrier is an oral thin film.

8. The composition of claim 7, wherein the composition is a layered construct comprising a first thin film, a second thin film, and the aggregate of microcapsules positioned between the first thin and the second thin film.

9. The composition of claim 8, wherein one of the first thin film and the second thin film is dissolvable under mouth conditions and the other is substantially non-dissolvable under mouth conditions.

10. The composition of claim 8, wherein both of the first thin film and the second thin film are dissolvable under mouth conditions and wherein under the same mouth conditions, one of the first thin film and the second thin film dissolves at a rate that is faster than the other by a rate of about 10% or greater.

11. The composition of claim 7, wherein the aggregate of microcapsules is dispersed in the oral thin film.

12. The composition of claim 1, wherein the hydraulic encapsulation is configured for controlled release of the internal phase from the external phase based upon the pressure differential between the internal phase and the external environment at the site of delivery.

13. The composition of claim 12, wherein the pressure differential is between the internal phase and saliva in the mouth of the user.

14. The composition of claim 1, wherein each microcapsule in the aggregate of microcapsules comprises about 50% to about 98% by weight of the internal phase material based on the total weight of the hydraulic encapsulation.

15. An oral strip comprising:
    at least a first thin film; and
    an aggregate of microcapsules each formed of an internal phase surrounded by an external phase in the form of a hydraulic encapsulation such that there is a pressure differential between the internal phase and an external environment at a site of delivery;
    wherein the internal phase is hydrophilic and comprises material selected from the group consisting of nicotine, flavorants, humectants, tobacco extracts, and combinations thereof; and
    wherein the external phase is hydrophobic, comprises a lipid, and forms a substantially wall-like structure that is pseudoplastic and is non-collapsible.

16. The oral strip of claim 15, wherein the aggregate of microcapsules is dispersed in the at least one first thin film.

17. The oral strip of claim 15, comprising a first thin film and second thin film, wherein the aggregate of microcapsules is positioned between the first thin and the second thin film.

18. The composition of claim 15, wherein each microcapsule in the aggregate of microcapsules comprises about 50% to about 98% by weight of the internal phase material based on the total weight of the hydraulic encapsulation.

* * * * *